United States Patent [19]

Howland

[11] Patent Number: 4,758,080

[45] Date of Patent: Jul. 19, 1988

[54] POINTSPREAD RETINOSCOPE

[75] Inventor: Howard C. Howland, Ithaca, N.Y.

[73] Assignee: Cornell Research Foundation, Inc., Ithaca, N.Y.

[21] Appl. No.: 943,027

[22] Filed: Dec. 18, 1986

[51] Int. Cl.$^4$ .............................................. A61B 3/10
[52] U.S. Cl. ..................................... 351/211; 351/205
[58] Field of Search ............... 351/205, 211, 217, 218, 351/221; 33/DIG. 8, 178 R

[56] References Cited

U.S. PATENT DOCUMENTS

| | | |
|---|---|---|
| 1,631,329 | 4/1925 | Patterson . |
| 2,331,591 | 9/1940 | Arnesen . |
| 2,501,438 | 3/1947 | Copeland . |
| 2,715,352 | 4/1954 | Jobe . |
| 3,136,839 | 6/1964 | Safir . |
| 3,639,041 | 2/1972 | Cornsweet . |
| 4,432,617 | 2/1984 | Itoh et al. . |

Primary Examiner—John K. Corbin
Assistant Examiner—P. M. Dzierzynski
Attorney, Agent, or Firm—Jones, Tullar & Cooper

[57] ABSTRACT

A simple pointspread retinoscope and method of retinoscopy is described. The retinoscope consists of a variable radius shield mounted on a light source, to provide variable eccentricity between the axis of the light source and the edge of the shield. The observer points the retinoscope light source at the eye of a subject, and observes the retinal reflex over the edge of the shield. If a crescent is observed, the shield is rotated to a larger radius location and the procedure repeated. The highest numbered radial step at which a crescent of light appears in the pupil provides the eccentricity of the light source, and from this value, the value of the radius of the pupil, and the value of the distance between the shield and the pupil the defocus of the subject eye can be determined.

12 Claims, 1 Drawing Sheet

POINTSPREAD RETINOSCOPE

BACKGROUND OF THE INVENTION

This invention was made with Government support under Grant No. NIH-ROI-EY-02994, awarded by the Department of Health and Human Services, National Institute of Health, National Eye Institute. The Government has certain rights in the invention.

The present invention relates, in general, to retinoscopy, and more particularly to an improved apparatus and method for measuring the plane of focus of a subject's eye with little or no cooperation from the subject.

The problem of evaluating the optical characteristics of the eye of a subject such as a small child, who is unable to cooperate with the testing procedure, is a substantial one, and a great deal of attention has been placed on the development of objective methods and apparatus for this purpose. An objective method is one wherein the subject's appraisal of the test is not essential to the measurement. One of the most commonly used devices for providing such measurements is the retinoscope, which generates a light beam in such a manner as to permit the observer to look along the beam axis toward whatever is illuminated. The beam of light is directed toward the subject's pupil so that the observer can view the pupil through an aperture and watch for a reflex action in the eye. A typical retinoscope is shown and described in U.S. Pat. No. 2,715,352.

The reflex action which is viewed through a retinoscope appears as an illumination of the pupil, and the characteristics of this reflex action enable the operator of the retinoscope to determine the location of the plane of focus of the eye. This, in turn, permits determination of whether the subject's eye is normal (emmetropic), is nearsighted (myopic), or is farsighted (hyperopic), and further to determine the degree of such near or farsightedness; that is, to evaluate the degree of defocus of the eye. This observation of the reflex action takes advantage of the fact that when a point source of light is directed into a subject's eye, the light will strike the retina in a point for a normal eye. However, for an ametropic eye; that is, for an eye that is not properly focused, the point source will appear as a blur spot on the retina. The reflex action of the retina will reproduce an image of that blur spot at a location near the light source, and at that location the reflex image may be viewed or otherwise detected. Whereas in the case of a normally focused eye, the reflex image will be essentially the same size as the source, for ametropic (non-focused eyes), the reflex image will be a defocused image of the blur spot, which will be larger than the source. This defocused image is called the "pointspread". The size of the image so obtained is a function of the degree of defocus of the eye, the distance of the source and the detector from the eye, the radius of the subject's pupil, and the lateral distance between the point source of light and the edge of the detector. This distance between the source and the edge of the detector may be referred to as the eccentricity of the source. Thus, by determining the size of the pointspread, the degree of defocus can be ascertained.

In copending application Ser. No. 896,705 of Howard C. Howland, filed Aug. 15, 1986, a device for measuring the pointspread utilizing infrared light and a scanning light source is disclosed. Although the apparatus and method disclosed therein work well and provide accurate results, it has been found that there is a need for an extremely simple, easy-to-use device which can be used as a screening tool for quick evaluations of large numbers of patients or which can be used to obtain rapid measurements of the amount of defocus of the eyes of infants in small children who often will not cooperate with the use of complex measurement devices.

SUMMARY OF THE INVENTION

It is, therefore, an object of the present invention to provide a simple, easily used, hand-held pointspread retinoscope for use in estimating the degree of defocus of a subject's eyes.

It is a further object of the present invention to produce a pointspread retinoscope which is hand held and which can be used as a screening tool to provide rapid estimates of eye defocus.

It is still another object of the invention to provide means for objective measurement of the optical characteristics of the eye of a subject who is unable to cooperate with the testing procedure and to provide a rapid estimate of the amount of defocus of the subject's eye.

Briefly, the present invention comprises a conventional pen light or other small, hand-held source of light for use in illuminating a patient's eye. Secured to the light source is a generally arcuate opaque shield having an outer peripheral edge which is formed in a spiral having a plurality of arcuate steps each having a different radius from the center of the shield. The shield is perpendicular to and coaxial with the axis of the light beam produced by the light source. The radial distance from the axis of the light source to each of the arcuate steps on the periphery of the shield is known, and these radial distances define the eccentricity of the light source with respect to each arcuate step.

To test the degree of focus of a subject's eye, the source of light is directed toward the subject's eye and the observer views the reflex action of the eye generally along the axis of the light beam, but over the arcuate step having the smallest radius, or eccentricity. The observer then notes whether or not a crescent of light appears in the subject's eye. This crescent is the reflex image of the blur spot which appears on the retina of a defocused eye. If such a crescent is observed, the observer rotates the shield to align the next larger radius arcuate step with the subject's eye and repeats the process. This is continued until the crescent is no longer visible, and the radius of the arcuate step when this occurs represents the eccentricity (E) of the light source from the edge of the shield. Since the working distance (A) between the subject's eye and the light source is known, the relative defocus D may be computed as follows:

$$D = E/2ARr(s) \qquad \text{(Eq. 1)}$$

where r(s) is the estimated size of the radius of the subject's pupil. This pupil size can be estimated from a standard pupil size comparison chart such as the J. G. Rosenbaum Pocket Vision Screener distributed by Smith, Miller and Patch, Inc., New Brunswick, N.J.

The pointspread retinoscope can be easily constructed, and is simple to use, thereby making it extremely attractive for vision screening, where large numbers of patients are reviewed to determine whether they have problems which require further, more detailed testing. In addition, the device is useful for measuring the degree of defocus of the eyes of infants and young children since the device is very easy to handle.

BRIEF DESCRIPTION OF THE DRAWINGS

The foregoing and additional objects, features and advantages of the present invention will become apparent to those of skill in the art from a consideration of the following detailed description of a preferred embodiment thereof, taken in conjunction with the accompanying drawings, in which.

DESCRIPTION OF PREFERRED EMBODIMENT

Figure 1:
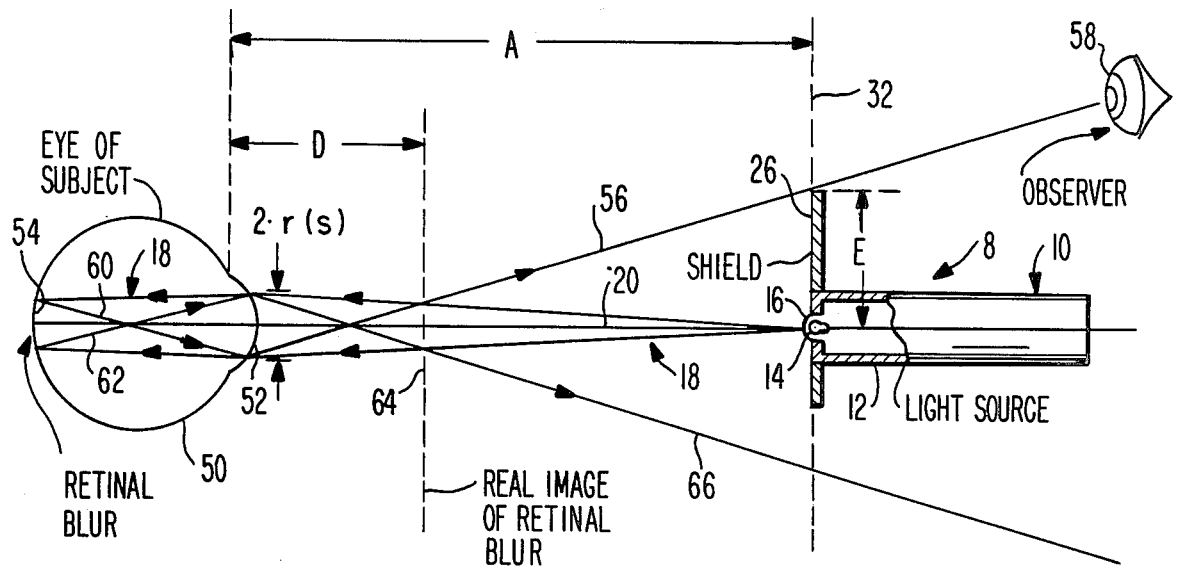
FIG. 1 is a diagrammatic illustration of the geometry of the optical relationships between the pointspread retinoscope of the present invention and the eye of a subject.

Turning now to a more detailed consideration of the drawings, the pointspread retinoscope generally indicated at 8 in each of the figures includes a light source 10 which may be a small, lightweight, battery-operated flashlight such as a conventional pen light. The pen light is diagrammatically illustrated in partial cross-section in FIG. 1, in perspective view in FIG. 2, and in end view in FIG. 3. The pen light includes a cylindrical housing carrying a bulb 14 and a lens 16 which produces a beam of light generally indicated at 18 in FIG. 1, the beam diverging from the light source axis 20 generally in the manner illustrated in the figure. The light source 10 may include a conventional push button switch 22 (not shown in FIG. 1) and may incorporate a clip 24 or other fastener.

Figure 2:
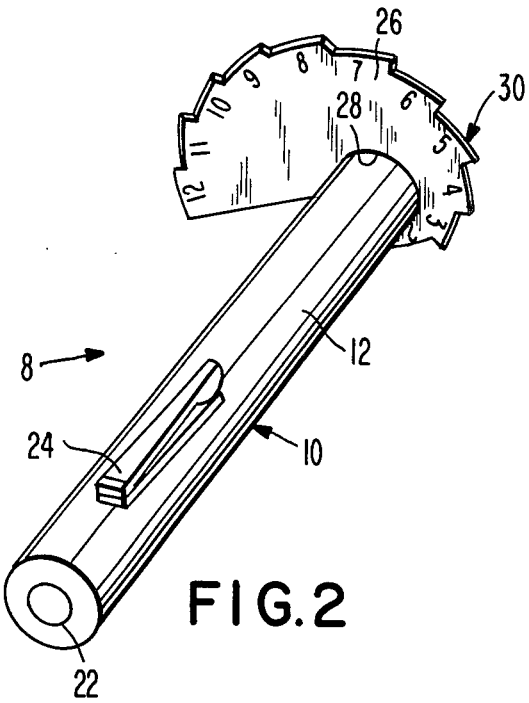
FIG. 2 is a perspective view of a pointspread retinoscope constructed from a pen light and shield, in accordance with the present invention.

Mounted on the end of the pen light housing 12, preferably adjacent the light bulb 14 and lens 16, is a retinoscope shield 26 which is used to measure the size of the retinal blur in the eye of a subject. The shield 26 is generally arcuate in shape, and preferably is an opaque thin, flat, rigid panel formed of metal, plastic, paper, cardboard or the like and having an axial aperture 28 and a stepped, generally spiral, peripheral edge 30. The aperture 28 preferably is circular and is of a size to allow the shield to fit snugly over the end of pen light housing 12, with the inner edge of aperture 28 snugly in engagement with the outer surface of housing 12 so that the shield 26 is held firmly in place on the pen light and so that the axis of aperture 28, and thus of shield 26, is coaxial with the axis 20 of the light source. The shield preferably is a panel of sufficient thickness and rigidity to insure that the front surface of the shield will lie in a plane 32 which is perpendicular to the axis 20 of the light source 10 as illustrated in FIG. 1. Alternatively, the shield may be adhesively secured to the face of the light source, with aperture 28 surrounding and coaxial with the light beam 18. The spiral peripheral edge of the shield 26 incorporates a series of arcuate steps 34 through 44, with each step being a segment of a circle of different radius. Each step is a different radial distance from the axis of the shield, and thus a different distance from the axis 20, the radius increasing from a minimum at step 34 to a maximum at step 44.

Figure 3:
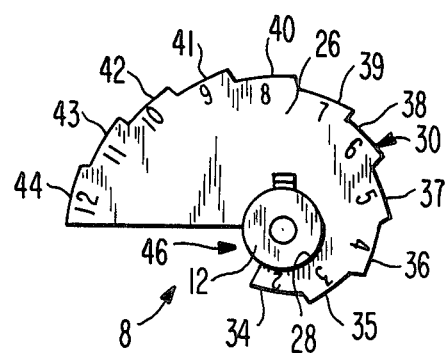
FIG. 3 is an end view of the device of FIG. 2.

It will be noted that in the preferred form of the invention the shield 26 does not complete a full circle around the barrel, or housing 12 of pen light 10, as illustrated in FIG. 3. This is preferred, since it leaves an open space 46 between the step 34 and the step 44 which can serve as an additional step having a radius equal to the radius of the barrel of the pen light or of the housing of any other light source that might be used. Alternatively, the shield 26 can be extended to completely surround the light source and to provide an additional step in the area generally indicated at 46 in FIG. 3.

A typical pen light housing will have a radius of approximately 6.9 mm, and this distance may be considered to be the radius of the first step in region 46 of the pointspread retinoscope of the invention in its preferred form. The second step, illustrated at 34 and consisting of the smallest radius step on the shield 26 preferably has a radius 3.9 millimeters larger than the diameter of the housing 12. Each of the successive steps 35–44 provide an incremental increase in radius of 2.54 mm (i.e., 1/10 inch). If desired, the step 34 could also provide an increase of 2.54 millimeters, but for purposes of strengthening the shield, and insuring that it will remain in place, the larger 3.9 mm step is preferred. With these preferred step increments, step 44 will have a radius of about 36.2 millimeters. The radial distance between the axis 20 and the outer edge of the individual steps is illustrated in FIG. 1 as the eccentricity E.

The use of the pointspread retinoscope of the present invention is illustrated in FIG. 1, wherein the light beam 18 from the light source 10 is directed into the eye 50 of a subject to be tested, the light passing through the pupil 52 of the eye and striking the retina 54. The light source 10 is held by the observer at a distance A which is an easily measurable distance and preferably is about 1 or 1.5 meters. This distance is a compromise between a lesser distance which would provide a closer view of the subject's pupil, and a greater distance which would minimize the interval about 0 degrees of relative defocus in which no reflex is seen. The smallest radius of the shield, 26 which may be the outer surface of housing 12 or may be a step 34, is aligned by the observer so that the observer's line of vision, indicated at 56, passes from the observer's eye 58 across the smallest radius of the shield 26 to the lowest part of the pupil 52 of the subject's eye. Then the retinoscope is illuminated by switching on the light bulb 14 to illuminate the retina 54. The meridan of the eye which is refracted by the light is defined by a plane passing through the center of the pen light lamp filament 14, the center of the step in shield 26 which the observer is aligning with the subject's pupil, and the pupil itself. This is a vertical plane lying in the plane of the drawing of FIG. 1, and may be referred to as the vertical meridan.

While the light is on, the observer notes whether or not a crescent appears in the pupil of the subject's eye, and if so whether it is at the top or the bottom of the subject's pupil. A crescent appearing at the top indicates that the eye is relatively hyperopic, while a crescent at the bottom indicates that the eye is relatively myopic. If a crescent is seen, the shield is rotated to a larger radial step, and the procedure is repeated. This is continued until the observer can no longer see the crescent over the edge of the shield, and the observer then notes the highest numbered radial step at which a crescent was still seen in the subject's eye. Then, the pupil size is estimated from a standard pupil size comparison chart. This information permits computation of the relative defocus D from Equation (1) above, since the eccentricity E is known from the numbered peripheral step, the distance A is known, and the pupil radius r(s) is known from the pupil chart.

In order to determine the empirical relationship between the observed crescent at maximum eccentricity and the actual defocus of the subject's eye, tests were conducted on an artificial eye equipped with a 5% reflecting paper retina. The artificial eye was focused at 1.5 meters, and then varying degrees of defocus were introduced in random order by placing one or another of 19 trial lenses 25 millimeters in front of the eye, the trial lenses having values ranging from plus to minus 4.5 diopters. The defocus caused by these lenses was computed, making allowance for the finite distance between the ophthalmic lens and the first principal plane of the lens of the artificial eye. Numerous measurements were made by several observers at various eye apertures (or pupil sizes) and at various light intensities. The results obtained showed an excellent correlation between the actual and measured degrees of defocus obtained through the use of the device of the present invention. An additional comparison with measurements made on the eyes of infants and young children yielded a significant correlation, as well.

The theory of the illumination of the subject retinoscopic image may be explained as follows. If the retina 54 of a subject 50 (FIG. 1) is illuminated by a point source 14 at a distance, A, from the subject's pupil 52, the total flux of light into the subject's eye is proportional to the square of the radius of the subject's pupil size, r(s). The entering light 18 forms an illuminated patch on the subject's retina 54 which re-radiates along lines 60 and 62 towards the subject's pupil. This re-radiated light forms a real image of the illuminated retinal patch somewhere in object space, as at plane 64, and its rays return to the general area of the point source, along lines 56 and 66. At the plane 32 of the point source the re-radiated light forms a patch known as the "double-pass pointspread", extending between lines 56 and 66 at plane 32. The total flux, F(p), of re-radiated light is again proportional to the square of the subject's pupil size. Thus:

$$F(p) \propto r(s)^4/A^2 \quad (Eq.\ 2)$$

It is known that the radius of the double pass pointspread is given by the equation:

$$R = r(s)*D*A \quad (Eq.\ 3)$$

Thus the area of the double pass pointspread is as follows:

where D is the dioptric defocus of the eye relative to the plane 32 of the retinoscope. Thus the average illumination of the pointspread function, found by dividing the flux by the area, is:

$$I(p) \propto \frac{r(s)^2}{D^2 A^4}, \quad (Eq.\ 5)$$

where D is the dioptric defocus of the eye relative to the plane of the light source.

It should be noted that the illumination of the pointspread function will vary systematically along the pointspread radius on plane 32. For example, in a diffraction limited eye, this variation is proportional to the area of overlap of two circles:

$$I \propto \left[ \left( \arccos \frac{x}{R} \right) - \frac{x}{R} * \sqrt{1 - \left( \frac{x^2}{R} \right)} \right] \quad (Eq.\ 6)$$

where: I is the intensity of the light at distance R from the point source along plane 32, and x may assume any value from zero to R. However, the illumination of any area of the pointspread will always be proportional to its average illumination.

If now an observer 58 views the pupil 52 of the subject 50 from the pointspread plane 32 with the observer's pupil radius equal to r(r), then the flux into the observer's eye will be proportional to the average illumination of the pointspread and the square of the oberver's pupil radius. The area of the image of the subject's pupil on the retina of the observer 58 will be inversely proportional to the square of the distance to the subject 50 and directly proportional to the subject's pupil radius. Thus the illumination I(i) of the image of subject's pupil on the retinoscopist's retina will be:

$$I(i) \propto \frac{r(r)^2}{D^2 A^2}. \quad (Eq.\ 7)$$

This implies that the brightness of the image of the subject's pupil seen by the observer will not vary with the subject's pupil size.

The image seen by the observer 58, if the radius of the observer's pupil is small in comparison to the diameter of the pointspread function, will be evenly illuminated and have the shape of the common area of two overlapping circles, i.e. the two adjacent circular segments. These two circles are (1) the pupil of the subject, and (2) the focus of all points projected from the circular illuminated patch of the subject's retina onto the subject's pupil (and adjacent area) by rays passing through the conjugate image of the observer's pupil in or behind the eye of the subject.

Thus, a simple pointspread retinoscope and method of retinoscopy have been described wherein the degree of defocus of an eye is estimated from the disappearance of the bright fundal, or retinal, reflex, or "crescent" in the eye of the subject when the distance, or eccentricity, between the light source and the eye of the observer is systematically increased. The instrument is particularly suitable for large scale screening because it is easy to use and can be constructed from inexpensive materials.

Although the invention has been described in terms of a preferred embodiment, it will be apparent that numerous modifications and variations may be made without departing from the true spirit and scope thereof, as set forth in the following claims.

What is claimed is:

1. A pointspread retinoscope, comprising:
   means for producing a beam of light along an axis; and
   generally arcuate shield means lying in a plane perpendicular to said axis, said shield means comprising a panel having a peripheral edge incorporating a plurality of steps of increasing distance from said axis to define a generally spiral shield edge, each step defining a different eccentricity from said axis.

2. The retinoscope of claim 1, wherein said steps of said peripheral edge of said shield means are each segments of circles of different radius from said axis.

3. The retinoscope of claim 2, wherein each said step along said peripheral edge is a fixed increment larger than the next adjacent preceding step.

4. The retinoscope of claim 3, wherein said means for producing a beam of light comprises a housing containing a light source, and wherein said shield means is mounted on said housing.

5. The retinoscope of claim 4, wherein said plane perpendicular to said axis passes through said light source.

6. The retinoscope of claim 4, wherein said shield means includes an aperture for receiving said housing, whereby said housing passes through said shield to support said shield coaxially with said beam.

7. The retinoscope of claim 1, wherein said generally arcuate shield means substantially surrounds said means for producing a beam of light.

8. The retinoscope of claim 1, wherein said means for producing a beam of light comprises a generally cylindrical pen light having a lamp at one end.

9. The retinoscope of claim 8, wherein said shield means is removably mounted on said one end of said pen light.

10. The retinoscope of claim 1, wherein said shield means includes a thin, flat panel having an axis, and further including means for mounting said panel coaxially on said means for producing a beam of light.

11. A method of measuring the defocus of a subject eye, comprising:
directing a beam of light from a source along an axis through the pupil and onto the retina of the subject eye, the reflex action of the subject eye producing a real image of the retinal blur line to the defocus of the subject eye;
positioning a generally spiral, stepped shield in a plane perpendicular to said axis, said shield including a plurality of steps each having a different eccentricity with respect to said axis;
aligning a selected step of said shield with the edge of the retina of the subject eye;
determining whether the reflex action of the subject eye produces an image of said beam of light visible over the said aligned step of said shield; and
aligning different steps of said shield as required to determine the eccentricity required to block the reflex image of said beam of light to thereby determine the amount of defocus.

12. The method of claim 11, further including:
positioning the shield at a distance A from the retina of the subject eye;
determining the radius r(s) of the pupil of the subject eye; and
determining the defocus D from the eccentricity required to block the reflex image of said beam of light in accordance with the relationship $$D = \frac{E}{2Ar(s)}.$$

* * * * *